(12) United States Patent
Wollenweber (10) Patent No.: US 9,684,973 B2
(45) Date of Patent: Jun. 20, 2017

(54) SYSTEMS AND METHODS FOR SELECTING IMAGING DATA FOR PRINCIPLE COMPONENTS ANALYSIS

(71) Applicant: General Electric Company, Schenectady, NY (US)

(72) Inventor: Scott David Wollenweber, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 171 days.

(21) Appl. No.: 14/563,047

(22) Filed: Dec. 8, 2014

(65) Prior Publication Data
US 2016/0163095 A1 Jun. 9, 2016

(51) Int. Cl.
| | |
|---|---|
| G06T 17/00 | (2006.01) |
| G06T 7/60 | (2017.01) |
| G06T 7/20 | (2017.01) |
| A61B 6/03 | (2006.01) |
| G01T 1/29 | (2006.01) |
| A61B 6/00 | (2006.01) |

(52) U.S. Cl.
CPC .............. *G06T 7/602* (2013.01); *A61B 6/037* (2013.01); *A61B 6/469* (2013.01); *A61B 6/5217* (2013.01); *A61B 6/5264* (2013.01); *A61B 6/5288* (2013.01); *G01T 1/2985* (2013.01); *G06T 7/20* (2013.01); *A61B 6/5205* (2013.01); *G06T 2207/10104* (2013.01)

(58) Field of Classification Search
None
See application file for complete search history.

(56) References Cited

U.S. PATENT DOCUMENTS

| | | | |
|---|---|---|---|
| 5,983,251 | A | 11/1999 | Martens et al. |
| 7,117,026 | B2 | 10/2006 | Shao et al. |
| 7,136,518 | B2 | 11/2006 | Griffin et al. |
| 7,367,953 | B2 | 5/2008 | Salla et al. |
| 7,680,240 | B2 | 3/2010 | Manjeshwar et al. |

(Continued)

OTHER PUBLICATIONS

Nehmeh, Sadek A., and Yusuf E. Erdi. "Respiratory motion in positron emission tomography/computed tomography: a review." Seminars in nuclear medicine. vol. 38. No. 3. WB Saunders, 2008.*
E.D. Brandner et al., "Abdominal organ motion measured using 4D CT", Int. J. Radiat. Oncol., Biol., Phys. 65(2), 554-560, 2006.
P.E. Kinahan et all; "Attenuation Correction for a combined 3D PET/CT Scanner", Med. Phys. 25(10), 2046-2053, 1998.

(Continued)

*Primary Examiner* — Vikkram Bali
*Assistant Examiner* — Tracy Mangialaschi
(74) *Attorney, Agent, or Firm* — Dean D. Small; The Small Patent Law Group, LLC (57) ABSTRACT

A method is provided that includes acquiring, with a detector defining a field of view (FOV), emission imaging data of an object over the FOV. The method also includes determining, with one or more processing units, a volume of interest (VOI) of the emission imaging data, wherein the VOI defines a volume smaller than an imaged volume of the object. Further, the method includes performing, with the one or more processing units, a multivariate data analysis on the VOI to generate a waveform for the VOI. Also, the method includes determining, with the one or more processing units, an amount of motion for at least the VOI based on the waveform. The method further includes displaying, on a display unit, at least one of the amount of motion or an image reconstructed based on the emission imaging data.

14 Claims, 4 Drawing Sheets

(56) References Cited

U.S. PATENT DOCUMENTS

| | | |
|---|---|---|
| 7,831,088 B2 | 11/2010 | Frakes et al. |
| 8,175,360 B2 | 5/2012 | Razifar et al. |
| 8,233,689 B2 | 7/2012 | Razifar et al. |
| 8,299,438 B2 | 10/2012 | Fenchel et al. |
| 8,411,915 B2 | 4/2013 | Wischmann et al. |
| 2005/0123183 A1 | 6/2005 | Schleyer et al. |
| 2010/0135556 A1 | 6/2010 | Razifar et al. |
| 2010/0303319 A1* | 12/2010 | Wang .............. G06T 11/006 382/131 |
| 2012/0281897 A1* | 11/2012 | Razifar ............ A61B 6/032 382/131 |
| 2013/0051643 A1* | 2/2013 | Jackson ............ G06T 11/006 382/131 |
| 2013/0294670 A1 | 11/2013 | Park et al. |
| 2016/0203599 A1* | 7/2016 | Gillies ............. G06T 7/0012 382/132 |

OTHER PUBLICATIONS

P Razifar et al; "Volume-Wise Application of Principal Component Analysis on Masked Dynamic PET Data in Sinogram Domain". IEEE Trans. Nucl. Sc. 53, 2759-68, 2006.

M. M. Osman et al.; "Clinically significant inaccurate localization of lesions with PET/CT: Frequency in 300 patients", J. Nucl. Med. Technol. 44, 240-243, 2005.

Y.E. Erdi et al., "PET-CT: The CT motion quantitation of lung lesions and its impact on PET-measured SUVs", J. Nucl. Med. Technol. 45, 1287-1292, 2004.

M. Dawood et al; "Respiratory Gating in positron emission tomography: A quantitive comparisioin of different gating schemes", Med. Phys. 34(7), 2007.

P. Razifar et al; "Principal Component Analysis with Pre-Normalization Improves the Signal-to-Noise Ratio and Image Quality in Positron Emission Tomography Studies of Amyloid Deposits in Alzheimer's Disease" Phys. Med. Biol. (54) 2009, 3595-3612.

* cited by examiner

FIG. 4 ously filed on Dec. 18, 2014.

SYSTEMS AND METHODS FOR SELECTING IMAGING DATA FOR PRINCIPLE COMPONENTS ANALYSIS

BACKGROUND OF THE INVENTION

The subject matter disclosed herein relates generally to imaging systems, and more particularly to methods and systems for selecting information for processing with a principal components analysis (PCA) technique or other method to derive a physiological waveform in conjunction with motion analysis (e.g., identification and/or mitigation of motion within imaging data).

During operation of medical imaging systems, such as PET imaging systems and/or multi-modality imaging systems (e.g., a PET/Computed Tomography (CT) imaging system, a PET/Magnetic Resonance (MR) imaging system), the image quality may be affected by motion of the object being imaged (e.g., a patient). In particular, motion of the imaged object may create image artifacts during image acquisition, which degrades the image quality. Respiratory motion is an example of a common source of involuntary motion encountered in medical imaging systems.

Motion artifacts in acquired imaging information may be addressed by various motion mitigation processing techniques. However, application of motion mitigation techniques may result in drawbacks, such as an increase in noise (e.g., by decreasing the signal-to-noise ratio due to discarding portions of the signal) and/or reduction of image quality resulting from the discarding of information.

BRIEF DESCRIPTION OF THE INVENTION

In an embodiment, a method includes acquiring, with a detector defining a field of view (FOV), emission data (e.g., positron emission tomography (PET) imaging data) of an object over the FOV. The method also includes determining, with one or more processing units, a volume of interest (VOI) of the emission imaging data, wherein the VOI defines a volume smaller than an imaged volume of the object. Further, the method includes performing, with the one or more processing units, a multivariate data analysis (e.g., a principle components analysis (PCA)) on the VOI to generate a waveform for the VOI. Also, the method includes determining, with the one or more processing units, an amount of motion for at least the VOI based on the waveform. The method further includes displaying, on a display unit, at least one of the amount of motion or an image reconstructed based on the emission imaging data.

In an embodiment, an emission imaging system is provided that includes a detector, a display unit, and at least one processing unit. The detector defines a field of view (FOV). The at least one processing unit is operably coupled to the detector and to the display unit and configured to acquire emission imaging data of an object over the FOV; determine a volume of interest (VOI) of the emission imaging data, wherein the VOI defines a volume smaller than an imaged volume of the object; perform a multivariate data analysis on the VOI to generate a waveform for the VOI; determine an amount of motion for at least the VOI based on the waveform; and displaying, via the display unit, at least one of information corresponding to the amount of motion or an image reconstructed based on the emission imaging data.

In an embodiment, a tangible and non-transitory computer readable medium is provided that includes one or more computer software modules configured to direct one or more processors to acquire, via a detector defining a field of view (FOV), emission imaging data of an object over the FOV; determine a volume of interest (VOI) of the emission imaging data, wherein the VOI defines a volume smaller than an imaged volume of the object; perform a multivariate data analysis on the VOI to generate a waveform for the VOI; determine an amount of motion for at least the VOI based on the waveform; and display at least one of information corresponding to the amount of motion or an image reconstructed based on the emission imaging data.

DETAILED DESCRIPTION OF THE INVENTION

The following detailed description of certain embodiments will be better understood when read in conjunction with the appended drawings. To the extent that the figures illustrate diagrams of the functional blocks of various embodiments, the functional blocks are not necessarily indicative of the division between hardware circuitry. For example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated, such as by stating "only a single" element or step. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

Various embodiments reduce computational requirements, reduce noise, increase image quality, and/or improve the usefulness of PCA results via the identification of one or more subsets of acquired imaging data to be used with a PCA utilized, for example in connection with motion mitigation, instead of performing a PCA only on an entirety of the imaging data, or on an entirety of imaging data within an imaging volume of a subject being imaged. For example, a mask may be applied to imaging data to remove data outside of a volume of interest (VOI). The imaging data may be acquired by a detector having a field of view (FOV), and a PCA used in connection with motion mitigation processing may be performed for the VOI specified by a manual input of a user. Additionally or alternatively, the VOI may be automatically generated, for example using a general anatomical model. It may be noted that the VOI may include a single contiguous volume (e.g., a single organ), or multiple, discrete volumes (e.g., multiple organs, lesions, or tumors, among others).

Various embodiments utilize a principle components analysis (PCA) in conjunction with identification and/or mitigation of motion in imaging data. Generally, a PCA approach may be utilized to determine the nature of variation in data. In emission tomography (e.g., PET), coincidence event data is typically acquired over a time period of several minutes per bed position. During this time, a patient will typically breathe over several cycles. The resulting respiratory motion may incur data-degrading blur. The motion-induced blur may result in the loss of feature conspicuity, lower quantitation accuracy, and/or general image quality degradation.

For example, as part of a conventional PCA motion mitigation approach, PET list-mode data may be down-sampled to coarse sinograms. The sinogram may be masked to remove data under a certain threshold (e.g., a certain percentage of a maximum value, such as a maximum value of a mean of a sinogram). The sinogram data may be filtered, and a PCA performed on the data to provide a waveform. The waveform may be analyzed to find one or more variations corresponding to motion, such as a cyclic motion (e.g., respiratory motion). Per-cycle triggers may be developed for use with motion mitigation techniques (e.g., discarding of information outside of a quiescent period; gating). The identified motion may then be addressed with a motion mitigation processing technique designed to reduce the effects of motion. However, such motion mitigation processing techniques may result in the discarding of information, which may result in increased noise and/or reduced image quality. In contrast to conventional approaches, various embodiments reduce the amount of information subjected to motion mitigation processing (or potentially subjected to motion mitigation processing) by performing a motion-related PCA on a limited subset of imaging information, such as a VOI including one or more component volumes specified by a user and/or automatically generated. For additional discussion regarding PCA techniques, see U.S. Pat. No. 8,600,132, entitled "Method and Apparatus for Motion Correcting Medical Images" issued Dec. 3, 2013, the entire content of which is hereby incorporated by reference.

In various embodiments, a keyhole PET reconstruction technique may be employed, with data from outside the VOI used as an input but not processed. Keyhole PET reconstruction techniques may be employed with iterative image reconstruction techniques. For additional discussion regarding keyhole PET reconstruction, see U.S. Pat. No. 7,680,240, entitled "Iterative Reconstruction of Tomographic Image Data Method and System" (referred to herein as the 240 Patent), issued Mar. 16, 2010, the entire content of which is hereby incorporated by reference.

In some embodiments, motion within a VOI (e.g., one or more organs) is estimated using a weighting approach to the VOI. For example, non-attenuation corrected information acquired during a PET scan may be co-registered with an anatomical simulation model (e.g., NCAT phantom) to form a weighted sinogram mask per organ or volume. (As used herein, a NCAT phantom is NURBS-based cardiac torso phantom, where a NURBS-based phantom is a non-uniform rational B-spline based phantom. See for instance Segars et al., Medical Physics 40 (4) 2013) The mask may be utilized as part of a PCA. For example, the mask may be added to a previous mask (e.g., a previous mask configured to remove data below a pre-determined signal strength). Various embodiments provide for multiple assessments of motion within a VOI based upon target areas, such as the lungs and/or liver.

Based on a particular patient and/or procedure or indication, areas of anatomy that may be more prone to motion or of more interest than other areas may be preferentially selected as part of the VOI and application of a PCA and/or motion mitigation. For example, respiratory motion typically has the most impact nearest the lung/diaphragm boundary but may also have impact up to the top of the lung and/or to the bottom of the bladder, for example. The motion impact, for example, to data inferior to the liver may be of minimal diagnostic interest for a particular application, and therefore the VOI may be tailored for a particular indication, with a PCA and/or motion mitigation applied only to areas of interest for which motion mitigation may be diagnostically worthwhile (e.g., the benefit of motion mitigation exceeds the potential noise or image quality costs). Various embodiments may utilize acquired emission data along with an anatomical model to generate motion impact estimates based upon organs and/or areas within a volume of patient scan data.

Various embodiments provide for improved addressing of motion in PET scanning, for example by performing a PCA and/or related motion mitigation on a specified VOI of diagnostic interest that forms a smaller subset of the imaging data for a volume acquired during a scan. A technical benefit of at least one embodiment includes reduction in noise and/or improvement in image quality by eliminating or reducing unnecessary or undesirable motion mitigation. A technical benefit of at least one embodiment includes improved data acquisition for PET scans likely to be affected by motion. A technical benefit of at least one embodiment includes maintenance of image quality for portions of an image volume not impacted by motion or for which motion mitigation is not diagnostically useful. A technical effect of at least one embodiment includes improvement or optimization of trade-offs between total scan time, image quality, and quantitation accuracy.

Figure 1:
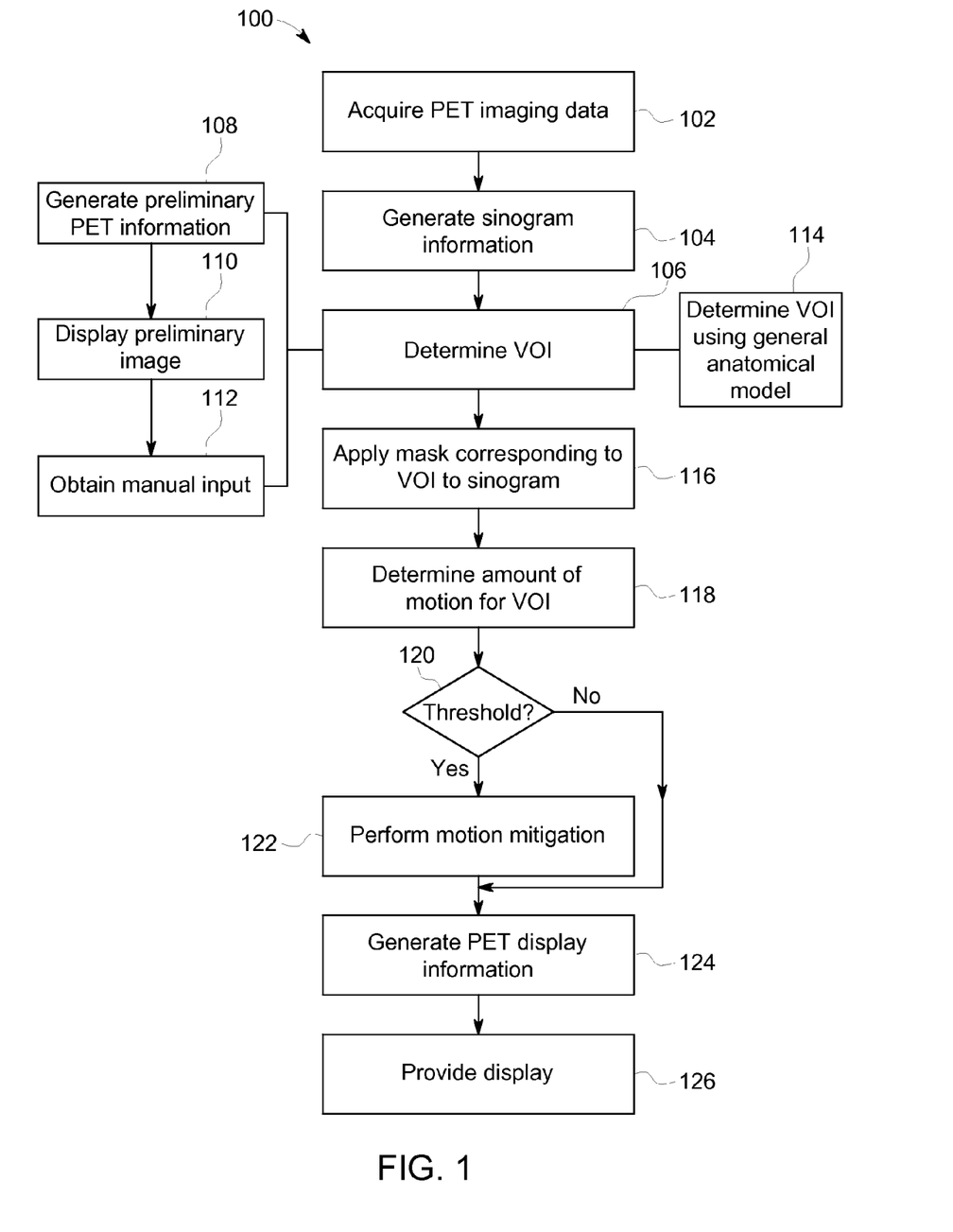
FIG. 1 is a flowchart of a method for PET imaging in accordance with various embodiments.

FIG. 1 provides a flowchart of a method 100 for imaging an object, in accordance with various embodiments. The method 100, for example, may employ or be performed by structures or aspects of various embodiments (e.g., systems and/or methods and/or process flows) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 100 may be able to be used as one or more algorithms to direct hardware (e.g., one or more processing units including one or more aspects of the motion mitigation module 494) to perform one or more operations described herein.

At 102, positron emission tomography (PET) imaging data (e.g., coincidence data) is acquired. The imaging data may be acquired, for example, using a PET detector (see, e.g., FIG. 4), and may be stored in a list of events ('list-mode'). In some embodiments, list-mode data may be stored for each coincident event (e.g., each event corresponding to detection by opposed portions of a PET detector, or each paired event), with a position (e.g., x and y), a time, and an energy level stored in list-mode for each coincident event. The detector used to acquire the PET imaging data defines a field of view (FOV) for the acquired imaging volume. For example, the FOV may be made up of positional FOV's from a plurality of bed positions. The detector may acquire information at a first bed position over a first FOV, at a second bed position over a second FOV, and so on. The FOV defined by the detector for the entire scan or acquisition may be determined by combining the positional FOV's from each bed position (accounting for any overlap between positional FOV's as appropriate). In some embodiments, the method 100 may be performed for each bed or detector position separately, with the FOV defined as the positional FOV for the given bed or detector position.

In various embodiments, the PET imaging data may be acquired using a cylindrical detector including rings of detector elements, with the detector advanced relative to a bed or table (e.g., the detector may be advanced and the bed or table fixed, or the bed or table may be advanced and the detector fixed) along an axial length of an object (e.g., human patient) to be imaged. The detector may be advanced in a step-and-shoot manner, in which the detector is advanced to a given detector or bed position along the axial length of an object, the detector is then stopped, information is acquired while the detector is stopped, and, following a desired amount of time for information acquisition, the detector is then advanced to one or more subsequent detector positions differently located along the axial length of the object to be imaged. Alternatively, the detector may be advanced continuously along the length of the object in some embodiments. This is functionally equivalent to continually advancing the object to be imaged relative to the detector. It may be noted that, while certain embodiments discussed herein are discussed in connection with PET, that other types or modalities of imaging data may be acquired or utilized additionally or alternatively in various embodiments. For example, in some embodiments, single photon emission computed tomography (SPECT) imaging data may be acquired. PET imaging data may be understood as one example of emission imaging data or emission data.

At 104 of the depicted embodiment, the list-mode data acquired at 102 is down-sampled or otherwise used to generate sinogram information. A sinogram is a typically generated as a sorted histogram of events in (r, theta, z) format and is most commonly used as a precursor of image reconstruction. A set of sinograms over time may also be formed. As used herein, "sinogram" is a general term implying counts of activity along Lines Of Response (LORs) of a detector. In general, the format of the segment data in various embodiments may be in one or more of a multitude of formats, including but not limited to sinograms, projection view data, Singles histograms, or coincidence event histograms, and is not necessarily restricted to a specific dimensional data set. The sinogram information may be generated at a coarse or reduced resolution, and may be utilized in conjunction with an initial PCA for generating preliminary information or a preliminary image. The preliminary information or preliminary image may be used to provide guide information (e.g., a preliminary image) from which a subset of information for a subsequent PCA is selected or otherwise determined. It may be noted that PCA is an example of a multivariate data analysis technique, and that other multivariate data analysis techniques may be employed additionally or alternatively in various embodiments. Examples of multivariate data analysis techniques include PCA, independent component analysis (ICA), and regularized PCA (rPCA).

Figure 2:
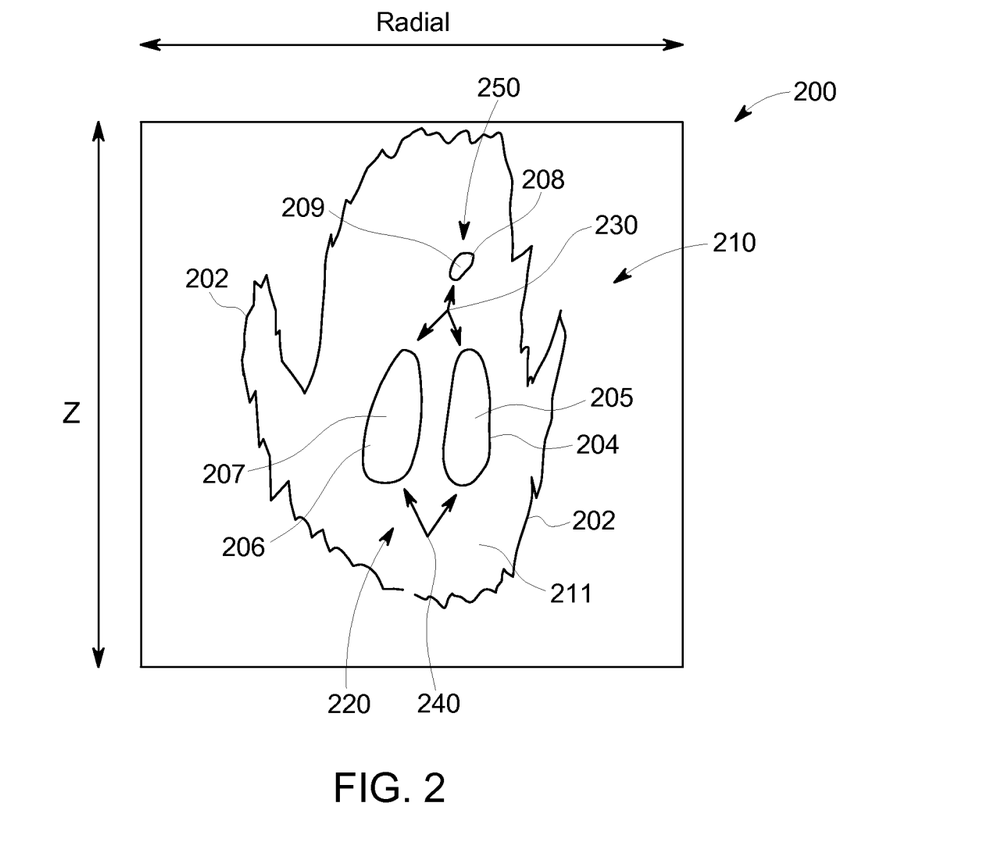
FIG. 2 provides a schematic view of a cut through a sinogram and masks in accordance with various embodiments.

For the initial PCA of the illustrated embodiment, a mask to reduce the impact of noise in the data may be employed. For example, FIG. 2 illustrates an example view 200 cut through a component of a sinogram, and displayed over a z-axis and a radial axis, in accordance with various embodiments. As seen in FIG. 2, the depicted sinogram includes a preliminary mask 202. The preliminary mask 202 may be applied during an initial or preliminary PCA to help separate information likely corresponding to noise or background from information likely corresponding to the object imaged. For example, after down-sampling of the list-mode data to generate a set of sinograms over time (e.g., a sinogram may be generated for every 0.5 seconds of list-mode data), a logical mask may developed to retain information that is within a predetermined range of a maximum signal or otherwise satisfies a threshold. For example, a mean value for the sinograms may be determined, and a mask applied to the data so that all data having a value equal or greater to a given percentage (e.g., 15%) of a maximum of the mean value for the sinograms may be retained while all other data are discarded. In FIG. 2, the information 220 on the interior of the mask 202 is retained and the information 210 on the exterior of the mask 202 is discarded. The information 220 on the interior of the mask 202 corresponds to the imaged volume of the object and may provide a guide set of information from which one or more subsets (VOI's) may be selected for additional processing (e.g., performance of one or more additional PCA's and/or motion mitigation processing).

Returning to FIG. 1, at 106, a volume of interest (VOI) is determined. Generally, the VOI includes one or more volumes for which additional processing (e.g., an additional PCA to be used in conjunction with determinations regarding motion mitigation) will be performed. Use of a VOI to define a smaller subset of information for further processing, in contrast to use of the entire FOV or imaging volume of the object, may reduce computational requirements and also minimizes or reduces the effect of drawbacks of motion mitigation, for example. The VOI may include a single, continuous volume, or as another example, may include a plurality of discrete volumes. For instance, the VOI may include a volume defined by locations or boundaries selected a user. Additionally or alternatively, the VOI may include volumes corresponding to one or more organs (e.g., lungs, liver). The particular VOI for a given application may be selected based on the indication or diagnostic purpose of the scan, and/or patient characteristics. For example, for an indication for which it is diagnostically useful to address motion in the lungs but not in the bladder, the lungs may be included in the VOI, with the bladder not included in the VOI.

With reference to FIG. 2, several example volumes which may be included in a single VOI and/or analyzed as separate VOI's are shown. As seen in FIG. 2, a first VOI mask 204 includes information 205, a second VOI mask 206 includes information 207, and a third VOI mask 208 includes information 209. The information for each depicted VOI may be understood as the imaging data for the object contained within a volume defined by the boundary of the corresponding VOI mask (or masks). In some embodiments, a VOI 230 may be defined as the combination of the first VOI (or, the VOI corresponding to the first VOI mask 204), the second VOI, and the third VOI. In other embodiments, one or more of the depicted VOI's may be considered as a separate VOI. For example, the first VOI and the second VOI may be combined into a single VOI 240 for a first PCA motion mitigation analysis, and the third VOI may be considered as a different VOI 250 for a second PCA motion mitigation analysis. A VOI (or portion thereof) may correspond to an organ, or may correspond to a different feature of interest, such as a lesion or tumor.

In various embodiments, the VOI (or VOI's) may be selected automatically or autonomously (e.g., based at least in part on particular patient and/or diagnostic purpose of the scan). Additionally or alternatively, a user input may be utilized as part of the determination of a VOI.

Returning to FIG. 1, sub-steps 108, 110, and 112 provide an example of obtaining a manual input, and determining the VOI based on the manual input. In the illustrated embodiment, at 108, preliminary PET information is generated for display. For example, the preliminary PET information may include one or more preliminary images generated for the FOV without motion mitigation. The preliminary images may be generated using a preliminary or initial PCA, which may utilize a preliminary or initial mask (e.g., initial mask 202) as discussed herein. The preliminary image, for example, may be a non-attenuation corrected image. Generally, the preliminary image may be generated at a resolution lower than a diagnostic resolution, as the preliminary image may be utilized to generally identify one or more VOI's for additional processing, and a high resolution may not be required to identify general areas or volumes. At 110, the preliminary image (e.g., a static PET image or non-motion mitigated image) is displayed to a user. One or more images (e.g., a 3D image and/or a group of 2D images) may be displayed to the user, for example on a screen (e.g., a touchscreen). At 112, a manual input is provided. For example, a user may use a finger or a stylus to circle one or more portions of interest of a displayed image(s). The selected portion(s) may then be determined as the VOI and a mask corresponding to the selected portions developed for use with a PCA used in conjunction with motion mitigation. For example, based on a known diagnostic purpose of the scan and the likelihood of respiratory motion affecting the lungs, motion mitigation for the lungs may be desired. Accordingly, a user may select, on the displayed image, a VOI corresponding to the lungs. As another example, a user may notice a potential lesion or tumor on a preliminary image, and/or have a priori knowledge of a likely location of a lesion or tumor, and may select a corresponding portion of the displayed image to be included in the VOI.

Additionally or alternatively, a VOI may be determined automatically or autonomously. For example, at 114 of the depicted embodiment, a general anatomical model is utilized to generate one or more VOI's. For example, a non-attenuation corrected image may be generated for the FOV or imaged volume of the object. Then, at least one model organ (e.g., one or more organs corresponding to a VOI) from the general anatomical model may be projected into an imaging volume of the FOV to provide model projection data, and a mask (e.g., first VOI mask 204) may be generated corresponding to the VOI using the model projection data. A motion mitigation PCA may be subsequently performed using the mask generated with the model projection data. (For additional discussion regarding use of a general anatomical model, see FIG. 3 and related discussion). The particular organs selected for inclusion in the VOI, projection into the imaging volume, and use in generating a VOI mask may be determined based on a user input (e.g., a user may select lungs, liver, bladder, or the like, and a VOI corresponding to the selected organs may be identified using an anatomical model), or may be determined autonomously (e.g., a processing unit may select one or more organs without user input, based for example on patient characteristics and/or a diagnostic purpose of the scan). In some embodiments, a preliminary VOI may be generated and presented to a user for approval, rejection, or modification before a final VOI is determined and used to generate a mask. For example, a VOI determined using sub-step 114 may be modified by a user, or may be added to or combined with a VOI determined using sub-steps, 108, 110, and 112. Thus, in some embodiments the VOI may be determined and a mask implemented autonomously, while in other embodiments a user input may be used.

At 116, a sinogram (e.g., a sinogram generated at 104) of at least a portion of the FOV (e.g., a sinogram to which a preliminary mask such as mask 202 has been applied) is masked using a mask corresponding to the VOI determined at 106. For example, the mask corresponding to the VOI may eliminate information not contained within a VOI (e.g., for the example of FIG. 2, information other than information 205, 207, and/or 209 may be eliminated by application of the mask corresponding to the VOI). Application of the mask corresponding to the VOI to the sinogram information provides masked imaging data which may be used in connection with a PCA utilized for motion mitigation in various embodiments. Accordingly, the proportion of imaging information of a FOV that is affected by motion mitigation processing may be reduced or minimized, thereby reducing computational resources and/or improving image quality by reducing drawbacks associated with motion mitigation processing.

At 118, an amount of motion for the VOI is determined. For example, in the illustrated embodiment, a PCA analysis is performed on the masked data provided at 116. Generally, a PCA may be performed for the VOI (or VOI's), and the value of one or more motion metrics determined. The analysis of the sinogram information with a PCA may be utilized to identify variations in time, for example to determine motion. In some embodiments, a cyclic variation, such as a respiratory motion, may be analyzed or identified using PCA. A PCA may be utilized to generate one or more one-dimensional waveforms that may be analyzed to determine corresponding motion. For example, repeated or cyclic variations in a PCA waveform (as used herein, a PCA waveform may be understood as a PCA-derived waveform or a waveform generated using a PCA or as part of a PCA) may be identified as corresponding to a repeated or cyclic motion occurring over a known similar cycle, such as respiratory motion. Additionally or alternatively, gross patient motion or non-cyclic motion may also be analyzed using a PCA waveform. One or more motion metrics may be determined using the PCA (or other computational technique) for a given VOI (e.g., a PCA performed on sinogram information to which a mask corresponding to the VOI has been applied). The metric may describe or correspond to an amount of respiratory motion. For example, in some embodiments, a respiratory motion magnitude 'R' may be determined, where R is the ratio of a peak in a respiratory frequency window to the mean above the window for a Fourier transform of a waveform generated using the PCA. Generally, in various embodiments, one or more motion metrics may be determined for a given VOI and used to determine whether or not motion mitigation processing is to be performed for the VOI.

At 120, it is determined if the amount of motion from a particular VOI determined at 106 satisfies a threshold. For example, if the amount of motion is equal to or greater than the threshold, the threshold may be satisfied and the method 100 may proceed to 122 for motion mitigation. However, if the amount of motion is less than the threshold, than the threshold may not be satisfied and the method 100 may proceed to 124. For example, in various embodiments where respiratory motion is to be addressed, the threshold may be a predetermined value of R as discussed herein, and the threshold value may be 15. Thus, if R for a given VOI is greater than or equal to 15, motion mitigation may be applied; however, if R is less than 15 than motion mitigation may not be applied for the VOI. The particular metric (or metrics) used, and/or the value (or values) thereof may be tailored for a particular application, so that VOI's exceeding a given amount of motion may have the motion addressed, while for VOI's not exceeding the given amount of motion, motion correction may be avoided. For example, for applications more diagnostically sensitive to respiratory motion, the R threshold may be lowered, or for applications less diagnostically sensitive to respiratory motion the R threshold may be increased. In the illustrated embodiment, for a VOI that satisfies the threshold (e.g., a VOI indicated as having sufficient motion for performance of motion mitigation processing), the method 100 proceeds to 122; however, for a VOI that does not satisfy the threshold (e.g., a VOI for which an amount of motion is determined insufficient to justify performance of motion mitigation processing), the method 100 proceeds to 124.

At 122, if the amount of motion for a VOI is determined to satisfy the threshold, motion mitigation is performed on the data for the VOI. Various motion mitigation techniques may be employed in various embodiments. For example, in some embodiments, PET coincident data for a VOI having motion above the threshold may be gated to produce 4D PET image volumes used to generate a motion mitigated image volume. In some embodiments, motion mitigation may involve a gating followed by image-based motion correction. In such embodiments, the VOI may be utilized to bound the sinogram data (e.g., via application of a mask), and a gating based upon the bounded data may be performed followed by motion correction of reconstructed PET image data (e.g., reconstructed image data generated using a keyhole reconstruction of the VOI). As another example, in some embodiments, data corresponding to the most quiescent portion of each respiratory cycle may be retained and used for imaging, with other data discarded and not used. For such embodiments, only the coincidence event data within a back-projection of the VOI onto the sinogram space may be considered as part of motion mitigation processing. It may be noted that various motion mitigation techniques may have costs or disadvantages associated therewith. For example, statistical quality of a resulting image or set of images may be lower per gate or within a quiescent bin due to the reduction of total data. Further, motion mitigation may degrade the quality of PET image data near a moving feature without a diagnostic benefit.

At 124 PET display information is generated, and at 126 a display is provided to a user (e.g., on a screen and/or print-out). In some embodiments the display information may be stored and/or communicated for subsequent analysis. The PET display information generated may be one or more reconstructed PET images. For example, a PET image for the FOV or the imaged volume of the object may be generated, using motion mitigation information as appropriate for the VOI within the FOV or the imaged volume of the object. Alternatively or additionally, the information generated, for example, may include one or more PCA waveforms and/or one or more motion metrics (e.g., R) for one or more organs or other locations within a VOI. In some embodiments, a first image may be generated employing motion mitigation processing on some or all of a VOI within the FOV, and a second image may be generated that does not employ motion mitigation techniques. The first and second images may then be displayed to a user to demonstrate the effect of motion on the images. It may be noted that, for embodiments where an image is reconstructed, a keyhole reconstruction technique (see, e.g., the 240 Patent for additional discussion on reconstruction techniques that may be employed in connection with various embodiments) may be employed. For example, information from the FOV not within the VOI (or not within another other smaller subset of information of the FOV) may be used as an input parameter when reconstructing the image; however only the information within the VOI (or other smaller subset of information of the FOV) may be processed.

As indicated above, in various embodiments, a general anatomical model may be used in connection with the determination of a VOI. An example of use of a general anatomical model is discussed in connection with FIG. 3.

Figure 3:
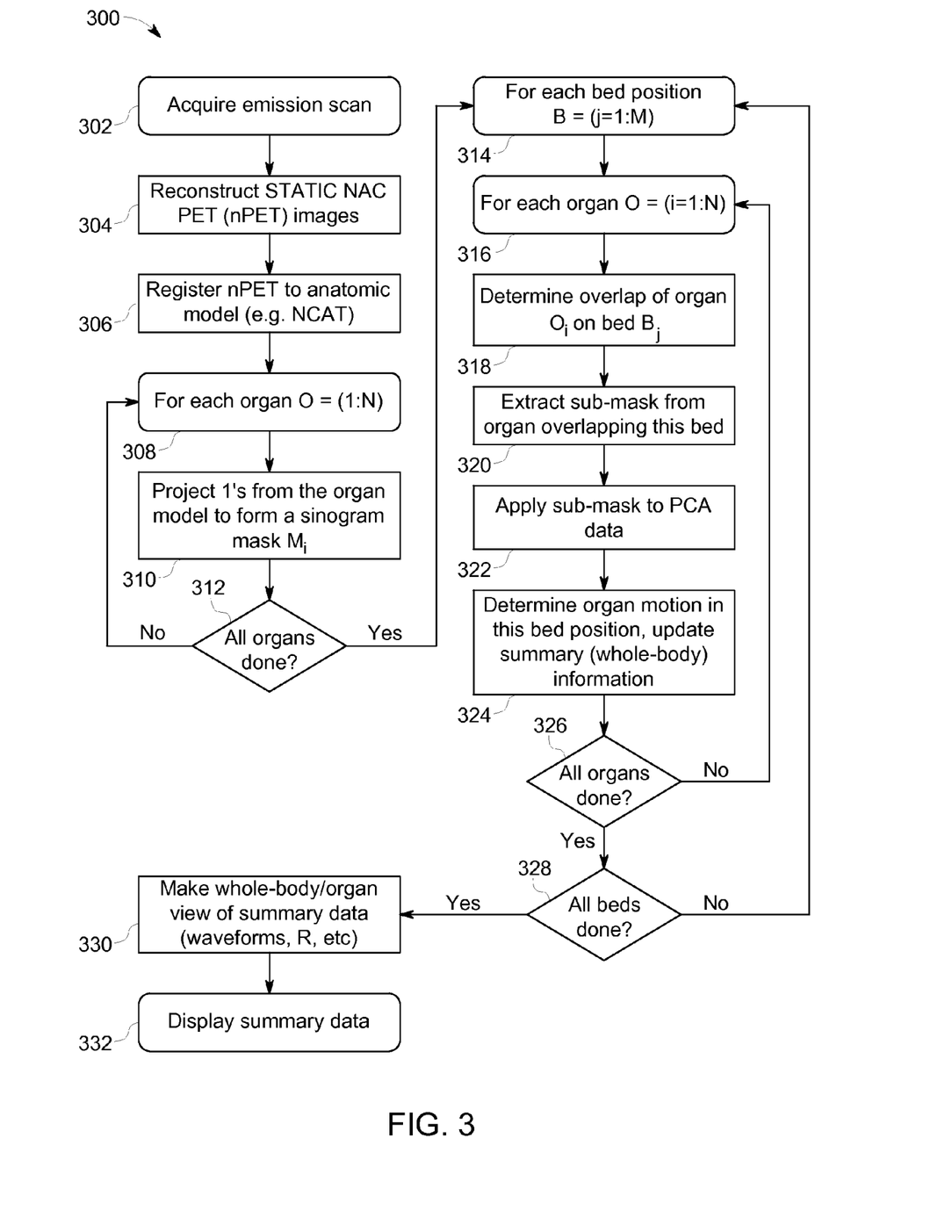
FIG. 3 is a flowchart of a method for PET imaging in accordance with various embodiments.

FIG. 3 provides a flowchart of a method 300 for imaging an object, in accordance with various embodiments. The method 300, for example, may employ or be performed by structures or aspects of various embodiments (e.g., systems and/or methods and/or process flows) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 300 may be able to be used as one or more algorithms to direct hardware (e.g., one or more processing units including one or more aspects of the motion mitigation module 494) to perform one or more operations described herein.

At 302, positron emission tomography (PET) imaging data (e.g., coincidence data) is acquired. The imaging data may be acquired, for example, using a PET detector (see, e.g., FIG. 4), and may be stored in a list-mode. In some embodiments, list-mode data may be stored for each coincident event (e.g., each event corresponding to detection by opposed portions of a PET detector, or each paired event), with a position (e.g., x and y), a time, and an energy level stored in list-mode for each coincident event. It may be noted that other emission imaging data, e.g., SPECT imaging data, may be additionally or alternatively acquired and utilized in various embodiments.

At 304, one or more non-attenuation corrected (NAC) images are generated using the PET imaging data acquired at 302. The NAC images may be generated as "static images." As used herein, a static image is an image for which motion mitigation processing techniques have not been applied.

At 306, the image(s) from 304 are registered to a general anatomical model. The static image(s) and the anatomical model may be co-registered. For example, the images may be registered to a model provided by the NCAT phantom simulation method. In various embodiments, such a registration facilitates projection of model organs from the model into a patient volume for the patient for a particular scan.

Next, using the organ projection data from 306, bed positions and/or different organs may be looped over to match the projection data (or sets of projection data) from the model with the measured data. In some embodiments, the measured patient data may be processed with a physiological waveform method (e.g., derivation of a respiratory waveform using a PCA based method). For example, a preliminary mask may be applied to emission sinogram data to define "inside body" data or an imaged volume of the object (e.g., by applying a mask that eliminates signal below a predetermined threshold). The post-body mask data may then be modified by multiplication with a per-organ or per-area mask (e.g., a mask based upon one or more VOI's).

For example, in the illustrated embodiment, organs may be looped through beginning at 308. Each of the organs looped through may be determined by a user input for example, or, as another example, may be identified based on a particular procedure or diagnostic purpose of a scan. For example, if, for a particular diagnostic purpose it is useful to address motion in the lungs and liver but not in the bladder, the lungs and liver may be selected as organs for further evaluation and the bladder not selected. In the illustrated embodiment, the selected organs (1:N) may define a VOI.

At 310, for a current organ, a projection is performed from the particular organ model to form a sinogram mask for the particular organ. For example, in the illustrated embodiment, 1's are projected from the organ model image (0's may be projected from portions of the model image not corresponding to an organ of interest). At 312, if there are remaining organs, the method 300 returns to 308. If masks for all organs have been formed at 310, the method 300 proceeds to 314.

At 314-328, each organ and bed position combination are looped through to determine data relevant to organ motion at each bed position. In the illustrated embodiment, a current bed position to be analyzed is set at 314 and a current organ (e.g., one of the organs previously analyzed at 308) is set at 316. Next, at 318, an overlap between the current organ and the current bed position is determined. At 320, a sub-mask from the current organ overlapping the current bed position is extracted, and, at 322, the sub-mask is applied to PCA data for the scan (or other physiological waveform data). The application of organ-specific or area-specific masks with PCA processing in various embodiments provides waveforms and metrics that are weighted toward data only in the target organs or areas. At 324, the organ motion for the current bed position is determined (e.g., using a metric such as R discussed herein), and added to summary data for motion for the whole body (or portion being scanned). At 326 and/or 328, if there are remaining bed positions and organ combination to be evaluated, the method 300 returns to 314 or 316, as appropriate. If all organ and bed position combinations have been evaluated, the method 300 proceeds to 330.

At 330, a whole-body (or portion thereof that has been scanned) view of the summary data is provided. For example, the summary data may be formed into composite waveforms (e.g., PCA waveforms) and/or metrics. As one example, a composite R or other metric representing respiratory signal strength in emission data may be formed. At 332, summary data is displayed. For example, values of R for one or more organs or area of interest may be displayed to a user. In some embodiments, values of R may be provided as part of an anatomical map, with various color or other identifying schemes used to display relative motion of organs of interest (e.g., organs or portions thereof with low amounts of motion in a first color, organs or portions thereof with intermediate amounts of motion in a second color, and organs or portions thereof with high amounts of motion in a third color). In some embodiments, all organs or areas of interest for which R (or other motion metric) exceeds a threshold may be identified as included in a VOI (e.g., a VOI determined at 106 of the method 100 discussed in connection with FIG. 1). In some embodiments, the display of summary data may be utilized by a user in making a manual selection of organs or volumes for inclusion in the VOI.

While the method 300 of the illustrated embodiment is discussed in connection with step-and-shoot motion, it may be noted that, in some embodiments, the method 300 (or aspects thereof) may be performed in connection with continuous bed motion. In some embodiments, a table of results (e.g., effect of respiratory impact on various organs or locations of interest) may be calculated and generated for display to a user. As another example, waveforms for particular organs or areas of interest may be displayed. Further still, organ or area-based waveforms or other results may be saved, for example, for comparison with other studies. Also, a calibration or normalization based upon height, size, and/or volume may be performed to address patient-size effects. In some embodiments, if previous imaging data for a particular patient is available, recently acquired scan data and motion information may be compared for consistency with the previously obtained results.

Figure 4:
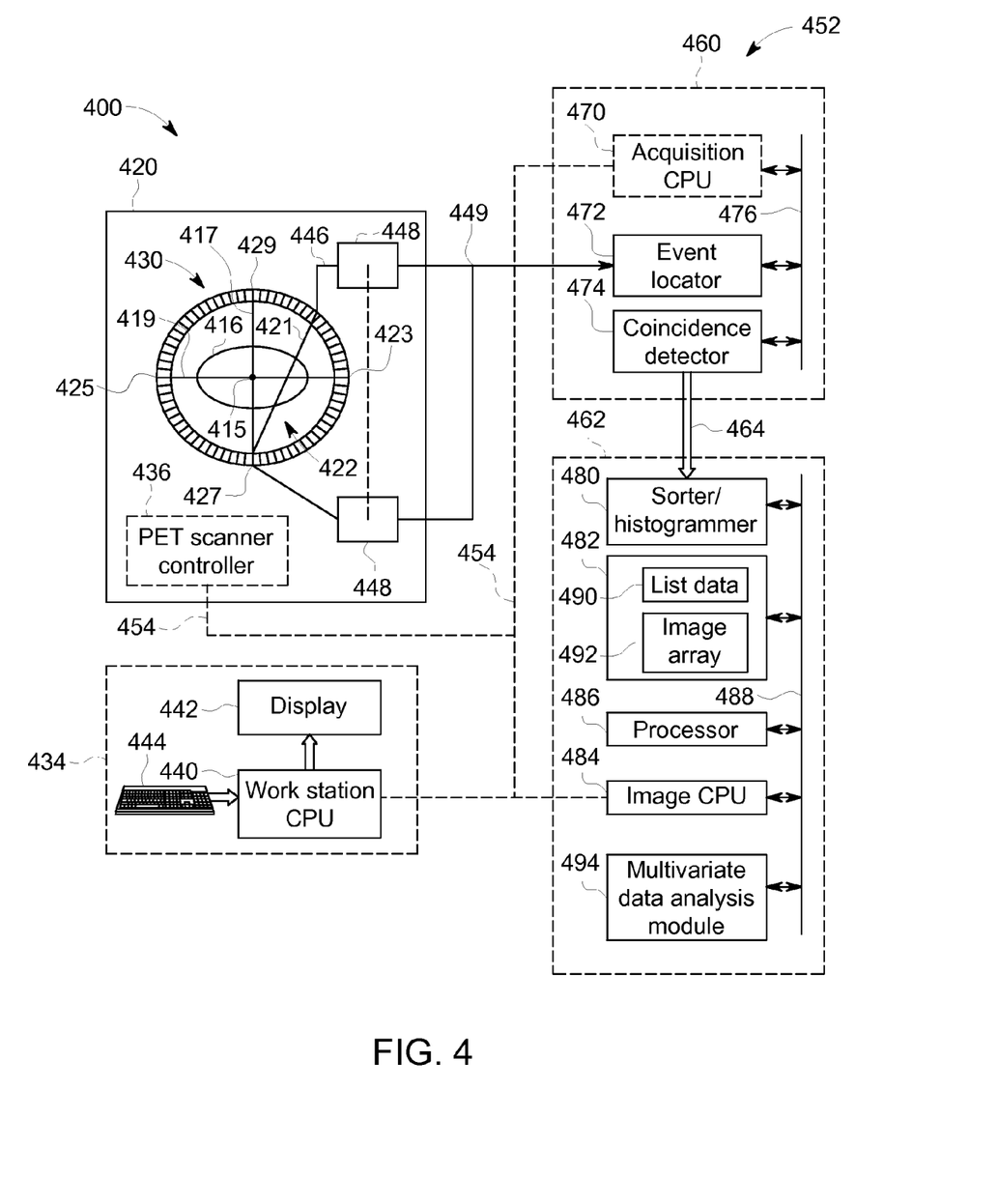
FIG. 4 provides a block diagram of a PET imaging system in accordance with various embodiments.

Various methods and/or systems (and/or aspects thereof) described herein may be implemented using a medical imaging system. For example, FIG. 4 is a block schematic diagram of an exemplary PET imaging system 400 that may be utilized to implement various embodiments discussed herein. The PET imaging system 400 may be used to acquire PET coincidence event data during a PET scan. The PET imaging system 400 includes a gantry, an operator workstation 434, and a data acquisition subsystem 452. In a PET scan, a patient 416 is initially injected with a radiotracer. The radiotracer comprises bio-chemical molecules that are tagged with a positron emitting radioisotope and can participate in certain physiological processes in the body of the patient 416. When positrons are emitted within the body, the positrons combine with electrons in the neighboring tissues and annihilate, creating annihilation events. The annihilation events usually result in pairs of gamma photons, with 511 keV of energy each, being released in opposite directions. The gamma photons are then detected by a detector ring assembly 430 within the gantry 420 that includes a plurality of detector elements (e.g., 423, 425, 427, 429). The detector elements may include a set of scintillator crystals arranged in a matrix that is disposed in front of a plurality of photosensors such as multiple photo multiplier tubes (PMTs) or other light sensors. When a photon impinges on the scintillator of a detector element, the photon produces a scintillation (e.g., light) in the scintillator. Each scintillator may be coupled to multiple photo multiplier tubes (PMTs) or other light sensors that convert the light produced from the scintillation into an electrical signal. In addition to the scintillator-PMT combination, pixilated solid-state direct conversion detectors (e.g., CZT) may also be used to generate electrical signals from the impact of the photons.

The detector ring assembly 430 includes a central opening 422, in which an object or patient, such as the patient 416 may be positioned, using, for example, a motorized table (not shown). The scanning and/or acquisition operation is controlled from an operator workstation 434 through a PET scanner controller 436. Typical PET scan conditions include data acquisition at several discrete table locations with overlap, referred to as 'step-and-shoot' mode. Optionally, during the PET scan, the motorized table may traverse through the central opening 422 while acquiring PET coincidence event data, for example, a continuous table motion (CTM) acquisition. The motorized table during the CTM acquisition may be controlled by the PET scanner controller 436. During the CTM acquisition, the motorized table may move through the central opening 422 at a consistent or stable velocity (e.g., within a predetermine velocity threshold during the PET scan).

A communication link 454 may be hardwired between the PET scanner controller 436 and the workstation 434. Optionally, the communication link 254 may be a wireless communication link that enables information to be transmitted to or from the workstation 434 to the PET scanner controller 436 wirelessly. In at least one embodiment, the workstation 434 controls real-time operation of the PET imaging system 400. The workstation 434 may also be programmed to perform medical image diagnostic acquisition in reconstruction processes described herein.

The operator workstation 434 includes a work station central processing unit (CPU) 440, a display 442 and an input device 444. The CPU 440 connects to a communication link 454 and receives inputs (e.g., user commands) from the input device 444, which may be, for example, a keyboard, a mouse, a voice recognition system, a touch-screen panel, or the like. Through the input device 444 and associated control panel switches, the clinician can control the operation of the PET imaging system 400. Additionally or alternatively, the clinician may control the display 442 of the resulting image (e.g., image-enhancing functions), physiologic information (e.g., the scale of the physiologic waveform), the position of the patient 416, or the like, using programs executed by the CPU 440.

During operation of the PET imaging system, for example, one pair of photons from an annihilation event 415 within the patient 416 may be detected by two detectors 427 and 429. The pair of detectors 427 and 429 constitute a line of response (LOR) 417. Another pair of photons from the region of interest 415 may be detected along a second LOR 419 by detectors 423 and 425. When detected, each of the photons produce numerous scintillations inside its corresponding scintillators for each detector 423, 425, 427, 429, respectively. The scintillations may then be amplified and converted into electrical signals, such as an analog signal, by the corresponding photosensors of each detector 423, 425, 427, 429.

A set of acquisition circuits 448 may be provided within the gantry 420. The acquisition circuits 448 may receive the electronic signals from the photosensors through a communication link 446. The acquisition circuits 448 may include analog-to-digital converters to digitize the analog signals, processing electronics to quantify event signals, and a time measurement unit to determine time of events relative to other events in the system 400. For example, this information indicates when the scintillation event took place and the position of the scintillator crystal that detected the event. The digital signals are transmitted from the acquisition circuits 448 through a communication link 449, for example, a cable, to an event locator circuit 472 in the data acquisition subsystem 452.

The data acquisition subsystem 452 includes a data acquisition controller 460 and an image reconstruction controller 462. The data acquisition controller 460 includes the event locator circuit 472, an acquisition CPU 470 and a coincidence detector 474. The data acquisition controller 460 periodically samples the signals produced by the acquisition circuits 448. The acquisition CPU 470 controls communications on a back-plane bus 476 and on the communication link 454. The event locator circuit 472 processes the information regarding each valid event and provides a set of digital numbers or values indicative of the detected event. For example, this information indicates when the event took place and the position of the scintillator crystal that detected the event. An event data packet is communicated to the coincidence detector 474 through a communication link 476. The coincidence detector 474 receives the event data packets from the event locator circuit 472 and determines if any two of the detected events are in coincidence.

Coincidence may be determined by a number of factors. For example, coincidence may be determined based on the time markers in each event data packet being within a predetermined time period, for example, 12.5 nanoseconds, of each other. Additionally or alternatively, coincidence may be determined based on the LOR (e.g., 417, 419) formed between the detectors (e.g., 423 and 425, 427 and 429). For example, the LOR 417 formed by a straight line joining the two detectors 427 and 429 that detect the PET coincidence event should pass through a field of view in the PET imaging system 400. Events that cannot be paired may be discarded by the coincidence detector 474. PET coincidence event pairs are located and recorded as a PET coincidence event data packet that is communicated through a physical communication link 464 to a sorter/histogrammer circuit 480 in the image reconstruction controller 462.

The image reconstruction controller 462 includes the sorter/histogrammer circuit 480. During operation, the sorter/histogrammer circuit 480 generates a PET list data 490 or a histogram, which may be stored on the memory 482. The term "histogrammer" generally refers to the components of the scanner, e.g., processor and memory, which carry out the function of creating the PET list data 490. The PET list data 490 includes a large number of cells, where each cell includes data associated with the PET coincidence events. The PET coincidence events may be stored in the form of a sinogram based on corresponding LORs within the PET list data 490. For example, if a pair of PET gamma photons are detected by detectors 427 and 429, the LOR 417 may be established as a straight line linking the two detectors 427 and 429. This LOR 417 may be identified as two dimensional (2-D) coordinates (r, θ, Δt), wherein r is the radial distance of the LOR from the center axis of the detector ring assembly 430, θ is the trans-axial angle between the LOR 417 and the X-axis, and Δt is the change in time of the detection of the photons between the two detectors 427 and 429 of the LOR 417. The detected PET coincidence events may be recorded in the PET list data 490. As the PET scanner 400 continues to acquire PET coincidence events along various LORs (e.g., 417, 419, 421), these events may be binned and accumulated in corresponding cells of the PET list data 490. The result is a 2-D sinogram λ(r, θ, Δt), each of which holds an event count for a specific LOR. In another example, for a three dimensional (3-D) sinogram, an LOR 417, 419 may be defined by four coordinates (r, θ, z, Δt), wherein the third coordinate z is the distance of the LOR from a center detector along a Z-axis.

Additionally, the communication bus 488 is linked to the communication link 452 through the image CPU 484. The image CPU 484 controls communication through the communication bus 488. The array processor 486 is also connected to the communication bus 488. The array processor 486 receives the PET list data 490 as an input and reconstructs images in the form of image arrays 492. Resulting image arrays 492 are then stored in a memory module 482. The images stored in the image array 492 are communicated by the image CPU 484 to the operator workstation 446.

The PET imaging system 400 also includes a motion mitigation module 494. The depicted motion mitigation module 494 is configured to perform one or more aspects, steps, operations or processes discussed herein (e.g., in connection with methods discussed in connection with FIG. 1 and/or FIG. 3.) For example, the motion mitigation module 494, and/or other aspect(s) of a processing unit, may be configured to identify a VOI of acquired information for which motion mitigation processing (e.g., including application of a PCA for use in connection with the determination of an amount of motion and/or the use of motion mitigation processing) may be applied.

The depicted motion mitigation module 494 is an example of a processing unit configured to perform one or more tasks or operations disclosed herein. A processing unit as used herein may include processing circuitry configured to perform one or more tasks, functions, or steps discussed herein. It may be noted that "processing unit" as used herein is not intended to necessarily be limited to a single processor or computer. For example, a processing unit may include multiple processors and/or computers, which may be integrated in a common housing or unit, or which may distributed among various units or housings.

It should be noted that the particular arrangement of components (e.g., the number, types, placement, or the like) of the illustrated embodiments may be modified in various alternate embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation may be particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optic drive, and the like. The storage device may also be other similar means for loading computer programs or other instructions into the computer or processor.

As used herein, the term "computer," "controller," "system," and "module" may each include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "module" or "computer."

The computer, module, or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer, module, or processor as a processing machine to perform specific operations such as the methods and processes of the various embodiments described and/or illustrated herein. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. Dimensions, types of materials, orientations of the various components, and the number and positions of the various components described herein are intended to define parameters of certain embodiments, and are by no means limiting and are merely exemplary embodiments. Many other embodiments and modifications within the spirit and scope of the claims will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph unless and until such claim limitations expressly use the phrase "means for" followed by a statement of function void of further structure.

This written description uses examples to disclose the various embodiments, and also to enable a person having ordinary skill in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal languages of the claims.

The foregoing description of certain embodiments of the present inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, or the like). Similarly, the programs may be stand alone programs, may be incorporated as subroutines in an operating system, may be functions in an installed software package, or the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

What is claimed is:
1. A method comprising:
   acquiring, with a detector defining a field of view (FOV), emission imaging data of an object over the FOV;
   determining, with one or more processing units, a volume of interest (VOI) of the emission imaging data, wherein the VOI defines a volume smaller than an imaged volume of the object, wherein the VOI is determined using a general anatomical model;
   reconstructing a non-attenuation corrected (NAC) image using the emission imaging data of the FOV;
   for each of multiple particular organs, performing a projection from a corresponding particular organ model to form a corresponding sinogram mask for the particular organ;
   performing, with the one or more processing units, a multivariate data analysis using the masks on the VOI to generate at least one waveform for the VOI;
   for each of plural bed positions, determining organ-specific motion data relevant to motion of each particular organ at each bed position;
   determining an amount of motion using the organ-specific motion data of each particular organ at each bed position;
   performing motion mitigation on the VOI based on the amount of motion, without performing motion mitigation on at least a portion of the FOV outside of the VOI, wherein the VOI is determined before performing the motion mitigation;
   reconstructing an image based on the emission imaging data; and
   displaying, on a display unit, at least one of information corresponding to the amount of motion or the image reconstructed based on the emission imaging data.

2. The method of claim 1, further comprising obtaining a manual input, and determining the VOI based on the manual input.

3. The method of claim 1, wherein performing the multivariate data analysis includes applying a mask to the emission imaging data of the FOV data to provide masked imaging data, wherein the mask corresponds to the FOV, and performing the multivariate data analysis on the masked imaging data.

4. The method of claim 1, further comprising determining if the amount of VOI motion exceeds a threshold and performing motion mitigation on the VOI if the amount of VOI motion exceeds the threshold.

5. The method of claim 4, wherein the motion mitigation comprises discarding of imaging data outside of a quiescent period.

6. The method of claim 4, wherein the motion mitigation is performed using gated bins.

7. An emission imaging system comprising:
   a detector defining a field of view (FOV);
   a display unit;
   at least one processing unit operably coupled to the detector and to the display unit and configured to
      acquire emission imaging data of an object over the FOV via the detector;
      determine a volume of interest (VOI) of the emission imaging data, wherein the VOI defines a volume smaller than an imaged volume of the object, wherein the VOI is determined using a general anatomical model;
      reconstruct a non-attenuation corrected (NAC) image using the emission imaging data of the FOV;
      for each of multiple particular organs, perform a projection from a corresponding particular organ model to form a corresponding sinogram mask for the particular organ;
      perform a multivariate data analysis using the masks on the VOI to generate at least one waveform for the VOI;
      for each of plural bed positions, determine organ-specific motion data relevant to motion of each particular organ at each bed position;

determine an amount of motion using the organ-specific motion data of each particular organ at each bed position;

perform motion mitigation on the VOI based on the amount of motion, without performing motion mitigation on at least a portion of the FOV outside of the VOI, wherein the VOI is determined before performing the motion mitigation;

reconstruct an image based on the emission imaging data; and displaying, via the display unit, at least one of information corresponding to the amount of motion or the image reconstructed based on the emission imaging data.

8. The emission imaging system of claim 7, wherein the at least one processing unit is configured to obtain a manual input, and to determine the VOI based on the manual input.

9. The emission imaging system of claim 7, wherein performing the multivariate data analysis includes applying a mask to the emission imaging data of the FOV data to provide masked imaging data, wherein the mask corresponds to the FOV, and performing the multivariate data analysis on the masked imaging data.

10. The emission imaging system of claim 7, further comprising determining if the amount of VOI motion exceeds a threshold and performing motion mitigation on the VOI if the amount of VOI motion exceeds the threshold.

11. A non-transitory computer readable medium comprising one or more computer software modules configured to direct one or more processors to:

acquire, via a detector defining a field of view (FOV), emission imaging data of an object over the FOV;

determine a volume of interest (VOI) of the emission imaging data using a general anatomical model, wherein the VOI defines a volume smaller than an imaged volume of the object;

reconstruct a non-attenuation corrected (NAC) image using the emission imaging data of the FOV;

for each of multiple particular organs, perform a projection from a corresponding particular organ model to form a corresponding sinogram mask for the particular organ;

perform a multivariate data analysis using the masks on the VOI to generate at least one waveform for the VOI;

for each of plural bed positions, determine organ-specific motion data relevant to motion of each particular organ at each bed position;

determine an amount of motion using the organ-specific motion data of each particular organ at each bed position;

perform motion mitigation on the VOI based on the amount of motion, without performing motion mitigation on at least a portion of the FOV outside of the VOI, wherein the VOI is determined before performing the motion mitigation;

reconstruct an image based on the emission imaging data; and display at least one of information corresponding to the amount of motion or the image reconstructed based on the emission imaging data.

12. The non-transitory computer readable medium of claim 11, wherein the computer readable medium is further configured to direct the one or more processors to obtain a manual input, and to determine the VOI based on the manual input.

13. The non-transitory computer readable medium of claim 11, wherein performing the multivariate data analysis includes applying a mask to the emission imaging data of the FOV data to provide masked imaging data, wherein the mask corresponds to the FOV, and performing the multivariate data analysis on the masked imaging data.

14. The non-transitory computer readable medium of claim 11, wherein the computer readable medium is further configured to direct the one or more processors to determine if the amount of VOI motion exceeds a threshold, and to perform motion mitigation on the VOI if the amount of VOI motion exceeds the threshold.

\* \* \* \* \*